United States Patent [19]

Do et al.

[11] Patent Number: 5,132,481
[45] Date of Patent: Jul. 21, 1992

[54] PROCESS OF METHANE OXIDATIVE COUPLING WITH HYDROGEN ACTIVATION OF CATALYST

[75] Inventors: Khac T. Do, New South Wales; James H. Edwards, East Ryde; Ralph J. Tyler, New South Wales, both of Australia

[73] Assignees: The Broken Hill Proprietary Company Limited, Melbourne; Commonwealth Scientific and Industrial Research Organisation, Australian Capital Territory, both of Australia

[21] Appl. No.: 545,948

[22] Filed: Jul. 2, 1990

[30] Foreign Application Priority Data

Jun. 30, 1989 [AU] Australia .................. PJ5021
Aug. 16, 1989 [AU] Australia .................. PJ5806

[51] Int. Cl.$^5$ .......... C07C 2/00; B01J 27/28; B01J 38/10
[52] U.S. Cl. .................. 585/500; 502/53; 502/174; 585/700; 585/943
[58] Field of Search .......... 502/53, 174, 340; 585/500, 700, 943

[56] References Cited

U.S. PATENT DOCUMENTS

| | | | |
|---|---|---|---|
| 1,945,960 | 2/1934 | Winkler et al. | 585/943 |
| 2,683,726 | 7/1954 | McGrath et al. | 502/174 |
| 3,432,572 | 3/1969 | Tazuma et al. | 502/174 |
| 3,758,673 | 9/1973 | Buben et al. | 502/174 |
| 3,875,298 | 4/1975 | Coafhey et al. | 423/637 |
| 4,450,310 | 5/1984 | Fox et al. | 585/943 |
| 4,658,077 | 4/1987 | Kolts et al. | 585/541 |
| 4,704,487 | 11/1987 | Devries | 585/943 |
| 4,727,212 | 2/1988 | Gaffney | 585/973 |
| 4,795,849 | 1/1989 | Gaffney et al. | 585/585 |
| 4,985,385 | 1/1991 | Williams et al. | 502/84 |
| 4,996,382 | 2/1991 | Matsuura et al. | 585/943 |

FOREIGN PATENT DOCUMENTS 63626  3/1988  Japan .................. 502/174

OTHER PUBLICATIONS

"Oxidative Dimerization of Methane over BaCO$_3$, SR CO$_3$ and These Catalysts promoted with Alkali" by -Ken-Ichi Aika et al.
J. Chem. Soc., Chem. Commun.—1986 pp. 1210–1211.
*Nature* 329 (Oct. 8, 1987) pp. 527–529 "Formation of Organic Carbon Compounds from Metal Carbonates'-'-A. Reller et al.

*Primary Examiner*—Paul E. Konopka
*Attorney, Agent, or Firm*—Nikaido, Marmelstein Murray & Oram

[57] ABSTRACT

The activation of catalysts which include carbonate compounds is brought about by exposing the catalyst to an atmosphere containing hydrogen. The invention is useful for activating Group IIA carbonates, such as strontium carbonate, for use in the oxidative coupling of methane.

9 Claims, 1 Drawing Sheet

PROCESS OF METHANE OXIDATIVE COUPLING WITH HYDROGEN ACTIVATION OF CATALYST

FIELD OF THE INVENTION

The present invention relates to a method for activating a catalyst of the type which exist, during the catalysed reaction, in both an oxide and a carbonate form.

PRIOR ART

It is known that the oxides and carbonates of a number of elements, and particularly Group IIA elements, have catalytic properties. The catalytic properties are particularly useful for the oxidative coupling of methane to form higher hydrocarbons.

In a co-pending patent application entitled "Oxidative coupling catalyst for methane" it is disclosed that it is necessary to destabilise the carbonate form of the Group IIA elements to enhance the catalytic activity of the catalyst. It is believed that the activity of these catalysts involves the formation of an oxide ion at the surface of the catalyst. Under reaction conditions in the presence of carbon dioxide, those active sites tend to form carbonates resulting in the loss of activity unless the temperature is raised above the carbonate dissociation temperature or constituents, such as clay, are present which destabilise the carbonates.

It is known from Reller et al., (Nature Vol. 329 p. 527, Oct. 8, 1987) that in a hydrogen atmosphere the thermal degradation of metal carbonates is observed at a comparably low temperature.

The present inventors have now found a new method whereby the catalysts of the type which exist in both an oxide form and a carbonate form during the catalysed reaction may be activated.

DISCLOSURE OF THE INVENTION

The present invention consists in a method for activating a catalyst which catalyst includes a compound capable, under the conditions of the catalysed reaction of existing in both the form of an oxide and the form of a carbonate, which method comprises exposing the catalyst to an atmosphere containing hydrogen.

The catalyst preferably contains oxides and carbonates of Group IIA elements, more preferably the Group IIA elements are strontium, calcium and barium. These catalysts may be promoted by the addition of oxides or carbonates of Group IA elements.

These catalysts are particularly useful as oxidative coupling catalysts for use in the conversion of methane to higher hydrocarbons. However, the oxides tend to react with carbon dioxide which is unavoidably produced during methane conversion. If the carbon dioxide partial pressure in the reactor is higher than the corresponding carbonate dissociation pressure at the reaction temperature, then the conversion of the catalysts to the carbonate form results in a reduced activity for the methane coupling reaction.

In order to retain the catalyst in its oxide form in a large scale methane conversion reactor, it would be necessary to continuously reactivate the catalyst by thermally decomposing the carbonate at the same rate at which it is formed in the reaction zone. However, in order to achieve reasonable carbonate decomposition rates it would be necessary to heat the catalyst at temperatures which are substantially higher than those employed for methane conversion. This would need to be conducted in a separate reactor and would require costly and complicated catalyst heating and cooling steps which would render a large scale process impractical.

The application of this activation technique to catalysts of the Group IIA oxides and carbonates provides acceptable rates of carbonate decomposition at temperatures employed for methane conversion. A feature of this discovery is that, unlike carbonate decomposition in inert atmosphere where only carbon dioxide is produced, the decomposition in the presence of hydrogen produces predominantly carbon monoxide. This has important implications for a large scale process using this discovery since it enables the major part of the hydrogen required for carbonate decomposition to be produced directly from this carbon monoxide by the well established water-gas shift method.

The catalyst is preferably exposed to the hydrogen at a temperature of at least 700° C., preferably between 700° C. and 1000° C. the catalyst should be exposed to the hydrogen for a period sufficient to convert at least a proportion of the carbonate to the corresponding oxide. The hydrogen containing atmosphere may comprise pure hydrogen or a mixture of gases containing at least 10% v/v of hydrogen.

In a further aspect the present invention consists in an activated catalyst produced by the method according to the present invention.

The discovery that hydrogen promotes the decomposition of carbonates, such as the Group IIA carbonates, has permitted the development of apparatus for conducting the oxidative conversion of methane using catalysts comprising an oxide of a Group IIA element.

Therefore, according to a third aspect of the present invention there is provided apparatus for the oxidative coupling of methane which apparatus comprises an oxidative coupling reactor containing a Group IIA carbonate catalyst, means for withdrawing a product gas and used catalyst from the reactor, a separator for separating the catalyst from the product gas, a catalyst regenerator for passing a hydrogen containing gas over the used catalyst, means for recycling the regenerated catalyst to the reactor and means for feeding methane and oxygen to the reactor.

A preferred type of coupling reactor is some form of fluidised bed or entrained flow reactor. An example of a suitable catalyst separator is a cyclone separator and the catalyst regenerator is preferably a fluidised bed or moving burden type reactor.

BRIEF DESCRIPTION OF THE DRAWINGS

An embodiment illustrating the present invention will now be described with reference to the accompanying drawing.

BEST MODE OF CARRYING OUT THE INVENTION

Figure 1:
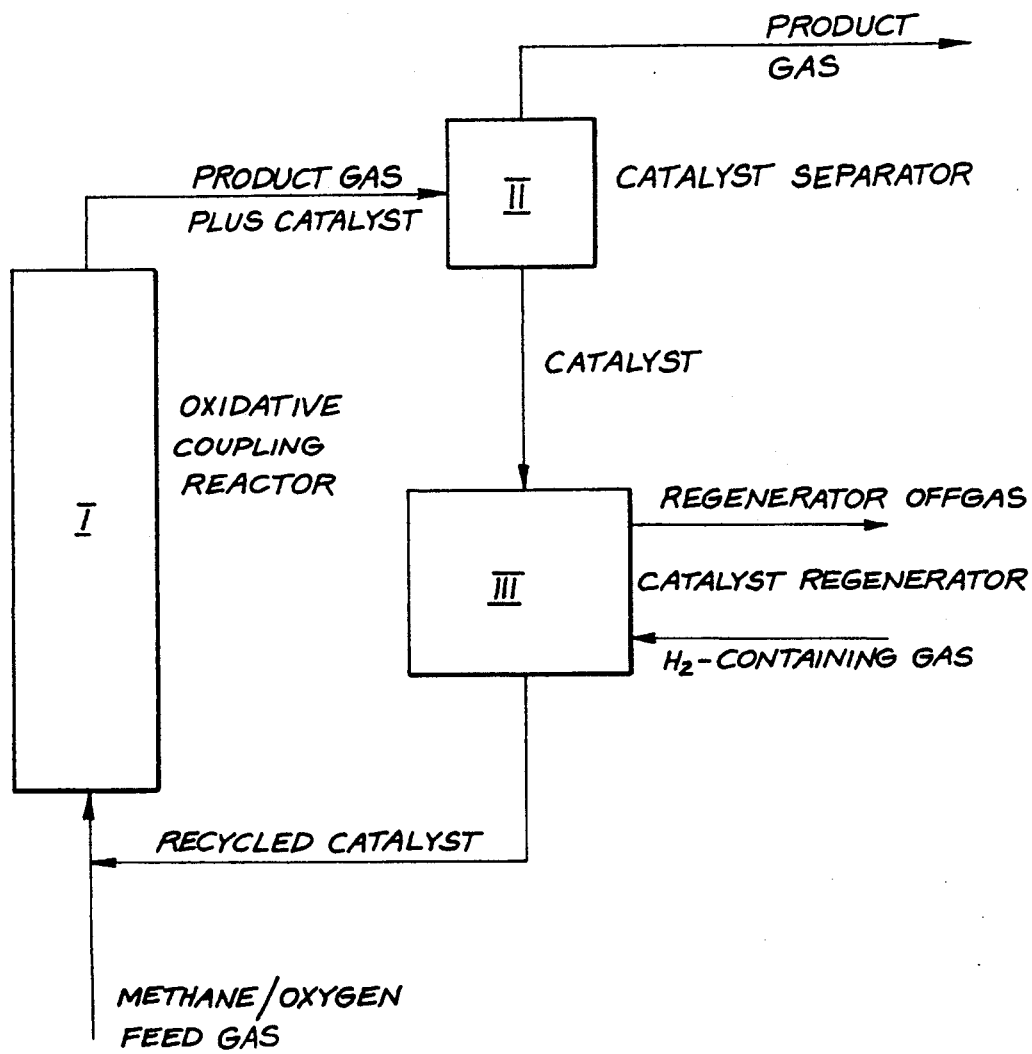

Methane and oxygen are fed to the oxidative coupling zone (I) of the reactor where they are contacted with catalyst which is initially in its highly active and selective oxide form. During the coupling process in the reactor, the catalyst is at least partially converted to the less desirable carbonate form as a result of reacting with carbon dioxide generated by the coupling reaction. The coupling reactor is designed in such a way that the catalyst particles can be continuously withdrawn from the reaction zone with the product gas as shown in FIG. 1. The combined product gas/catalyst stream is then passed to a catalyst separator (II) where the catalyst particles are recovered from the gas. The partially deactivated catalyst is then passed to the catalyst regenerator (III) where it is contacted with a hydrogen containing gas stream to convert it back to the oxide form by decomposition of the carbonate. The regenerated catalyst is then continuously returned to the conversion reactor (I) to complete the catalyst recirculation cycle.

The regeneration gas can be any gas stream containing hydrogen but a preferred source of hydrogen is hydrogen produced from the water-gas shift conversion of the carbon monoxide generated by the carbonate decomposition. Any additional hydrogen necessary for the regeneration process could be obtained from the hydrogen generated by the methane conversion reactions.

The enhanced rate of decomposition of carbonate in the presence of gaseous hydrogen is illustrated by the following example:

EXAMPLE 1

45g of catalyst ($-250+150$ um size) consisting of a mixture of strontium carbonate and magnesium oxide (containing 21.5% w/w strontium) was fluidised in nitrogen gas at 870° C. The gases from the fluidised bed reactor were monitored continuously for carbon oxides (both carbon dioxide and carbon monoxide) using gas analysers. Carbon dioxide, resulting from the decomposition of strontium carbonate, was present in the product gas at the rate of 0.018 g-mol $h^{-1}$. There was no carbon monoxide evolved.

Immediately upon adding hydrogen to the fluidising gas at a level of 28% v/v hydrogen, the rate of carbon oxides evolution increased from 0.018 to 0.26 g-mol $h^{-1}$ consisting of 0.223 g-mol $h^{-1}$ carbon monoxide and 0.037 g-mol $h^{-1}$ carbon dioxide. The decomposition rate of the carbonate was thus increased by more than 14 times by the addition of this level of hydrogen to the fluidising gas. In contrast to the decomposition in nitrogen, where carbon dioxide was the sole gaseous product, the presence of hydrogen resulted in carbon monoxide constituting more than 85% of the carbon oxides.

The total amount of carbon oxides produced during these treatments was measured and it corresponded to that equivalent to the strontium carbonate contained in the catalyst, indicating that complete decomposition of the carbonate had occurred.

EXAMPLE 2

The discovery that $H_2$ accelerated the decomposition of $SrCO_3$ has been used to conduct experiments in a fluidised bed reactor which have demonstrated a second feature of the current invention namely that catalysts containing strontium are superior methane coupling catalysts when the strontium is at least partly in the oxide rather than carbonate form under reaction conditions.

Catalyst consisting of a mixture of strontium carbonate and magnesium oxide containing nominally 22% w/w strontium was brought to reaction temperature by being fluidised in nitrogen. When the desired temperature was reached hydrogen was added to the fluidising nitrogen flow at a rate sufficient to give a hydrogen concentration in this gas stream of around 28% v/v. The product gas from the fluidised-bed reactor was monitored continuously for both carbon monoxide and carbon dioxide produced by the hydrogen-promoted decomposition of the strontium carbonate. This operation was continued until no measurable amounts of carbon oxides were present in the reactor effluent gas, at which stage the decomposition of the strontium carbonate to the oxide form was complete. At this point the nitrogen and hydrogen flows were stopped and methane and oxygen introduced to the reactor to conduct methane coupling tests with the strontium in the oxide form. Since these tests were conducted at temperatures where the partial pressure of the carbon dioxide produced by the methane coupling reaction was above the dissociation pressure of strontium carbonate, essentially all of the carbon dioxide thus formed reacted with the strontium oxide to form strontium carbonate. The time taken for this transformation from oxide to carbonate form was sufficiently long to enable the methane coupling performance of the catalyst to be determined at one set of reaction conditions. This was done by measuring detailed product gas flow rates and compositions and calculating the carbon dioxide which was reacted with the catalyst during this period from elemental mass balances. When the transformation of the strontium oxide to carbonate was complete there was a sudden increase in the carbon oxides in the reactor effluent since the catalyst was no longer capable of reacting with the carbon dioxide. When the reactor reached stable operating condition methane coupling measurements were again conducted with the catalyst now in the carbonate form. On completion of these measurements the methane and oxygen flows were stopped and nitrogen and hydrogen flows reintroduced to the reactor to once again convert the catalyst back into the oxide form. In this manner, by alternating the catalyst between the oxide and carbonate forms a series of measurements of catalyst performance under a variety of reaction conditions was obtained. These are shown in Table 1 which clearly shows that under all conditions the oxide form of the catalyst was superior to the carbonate form in terms of activity and selectivity to hydrocarbons.

TABLE III 60 mm Fluidised-bed Reactor Performance Data with Strontium-Magnesium Oxide (21.5% w/w Strontium) Catalyst

| | Operating temp. regime | | | | | | | |
|---|---|---|---|---|---|---|---|---|
| | Low | | moderate | | | | high | |
| Strontium form in catalyst | O* | C= | O* | C= | O* | C= | O* | C= |
| Feed gas Oxygen (% v/v) | 5 | 5 | 5 | 5 | 19 | 19 | 19 | 19 |
| Methane (% v/v) | 95 | 95 | 95 | 95 | 81 | 81 | 81 | 81 |
| Temperature (°C.) | 637 | 637 | 741 | 745 | 790 | 802 | 866 | 854 |
| Methane conversion (%) | 6.3 | 2.0 | 9.1 | 5.7 | 25.7 | 20.0 | 25.5 | 22.2 |
| Oxygen consumption (%) | 99 | 40 | 100 | 100 | 100 | 100 | 100 | 100 |
| Selectivity to hydocarbons (%) | 57.0 | 13.0 | 80.2 | 53.6 | 59.0 | 47.0 | 58.8 | 54.3 |
| Hydrocarbon yield (%) | 3.6 | 0.26 | 7.3 | 3.1 | 15.2 | 9.4 | 15.0 | 12.0 |

*O, catalyst with strontium in oxide form
=C, catalyst with strontium in carbonate form

We claim:

1. A oxidative coupling reaction wherein methane is oxidatively coupled to form higher hydrocarbons and which reaction utilizes a catalyst which comprises a compound of a Group IIA element which, under the conditions of the reaction, is capable of existing in both the form of an oxide and in the form of a carbonate, the reaction being characterized in that at least part of the catalyst is periodically activated by exposure to an atmosphere containing hydrogen at a temperature of at least 700° C. and for a time sufficient to convert at least a portion of the catalyst existing in the form of the carbonate to the corresponding oxide.

2. A reaction as claimed in claim 1 in which the catalyst additionally contains a carbonate of a Group IA element.

3. An oxidative coupling reaction as claimed in claim 1 in which at least part of the hydrogen is produced by a water-gas shift conversion of carbon monoxide generated during the activation of a carbonate catalyst by exposure to hydrogen.

4. An oxidative coupling reaction as claimed in claim 3 in which the Group IIA compound is a compound of strontium, calcium or barium.

5. An oxidative coupling reaction as claimed in claim 4 in which the Group IIA compound is a compound of strontium.

6. An oxidative coupling reaction as claimed in claim 3, in which the hydrogen containing atmosphere contains at least 10% v/v of hydrogen.

7. An oxidative coupling reaction as claimed in claim 3, in which the Group IIA compound is a compound of strontium, calcium or barium.

8. An oxidative coupling reaction as claimed in claim 1 in which the hydrogen containing atmosphere contains at least 10% v/v of hydrogen.

9. An oxidative coupling reaction as claimed in claim 8 in which the temperature is between 700° C. and 1000° C.

* * * * *

UNITED STATES PATENT AND TRADEMARK OFFICE
CERTIFICATE OF CORRECTION

PATENT NO. : 5,132,481
DATED : July 21, 1992
INVENTOR(S) : Khac T. DO et al

It is certified that error appears in the above-indentified patent and that said Letters Patent is hereby corrected as shown below:

On the title page, Item [75], please add the third inventor's name -- Peter F. Nelson, New South Whales, Australia --.

Signed and Sealed this

Fourth Day of January, 1994

Attest:

BRUCE LEHMAN

Attesting Officer

Commissioner of Patents and Trademarks